(12) United States Patent
Kamada

(10) Patent No.: US 6,785,406 B1
(45) Date of Patent: Aug. 31, 2004

(54) IRIS AUTHENTICATION APPARATUS

(75) Inventor: Mikio Kamada, Kanagawa (JP)

(73) Assignee: Sony Corporation, Tokyo (JP)

(*) Notice: Subject to any disclaimer, the term of this patent is extended or adjusted under 35 U.S.C. 154(b) by 543 days.

(21) Appl. No.: 09/619,743

(22) Filed: Jul. 19, 2000

(30) Foreign Application Priority Data

Jul. 19, 1999 (JP) .......................................... P11-205221

(51) Int. Cl.⁷ .............................. G06K 9/00; G06K 9/20; G06T 7/00; A61B 3/14
(52) U.S. Cl. ...................... 382/117; 382/115; 340/5.53; 340/5.83; 396/18
(58) Field of Search ........................ 356/71; 340/5.53, 340/5.83; 902/3, 6; 396/18; 351/206; 382/115, 117

(56) References Cited

U.S. PATENT DOCUMENTS

| | | | | |
|---|---|---|---|---|
| 4,252,420 A | * | 2/1981 | Kohayakawa | 351/208 |
| 4,620,318 A | * | 10/1986 | Hill | 382/117 |
| 4,641,349 A | * | 2/1987 | Flom et al. | 382/117 |
| 5,016,282 A | * | 5/1991 | Tomono et al. | 382/117 |
| 5,291,560 A | * | 3/1994 | Daugman | 382/117 |
| 5,572,596 A | * | 11/1996 | Wildes et al. | 382/117 |
| 5,956,122 A | * | 9/1999 | Doster | 351/210 |
| 6,247,813 B1 | * | 6/2001 | Kim et al. | 351/206 |
| 6,285,780 B1 | * | 9/2001 | Yamakita et al. | 382/110 |
| 6,542,624 B1 | * | 4/2003 | Oda | 382/117 |
| 6,571,002 B1 | * | 5/2003 | Ogawa | 382/117 |
| 6,591,001 B1 | * | 7/2003 | Oda et al. | 382/117 |
| 6,714,665 B1 | * | 3/2004 | Hanna et al. | 382/117 |

* cited by examiner

Primary Examiner—Jingge Wu
Assistant Examiner—Ryan J. Hesseltine
(74) Attorney, Agent, or Firm—Jay H. Maioli

(57) ABSTRACT

An iris authentication apparatus performs authentication based on data generated from a human iris in which camera section and a signal processing section detect an iris state in the form of data. By using a database section, an iris data processing section detects whether the iris state is in a living body state. When the iris data processing section has detected that the iris state is in a living body state, it is judged that the detected data is effective. In this manner, the iris authentication apparatus can reliably prevent a third person from being authenticated by pretending to be a registered person by forging an iris pattern that is a non-living-body iris.

2 Claims, 3 Drawing Sheets

IRIS AUTHENTICATION APPARATUS

BACKGROUND OF THE INVENTION

1. Field of the Invention

The present invention relates to an iris authentication apparatus that performs authentication based on data that is generated from an iris.

2. Description of the Related Art

Conventionally, fingerprint authentication apparatuses using data that is based on the pattern of a fingerprint that is part of a human body are in practical use.

Those fingerprint apparatuses operate in the following manner. A person who wants to be authenticated brings his fingerprint portion, the fingerprint of which was registered in advance in the authentication apparatus, into contact with a fingerprint reading portion of the authentication apparatus. The authentication apparatus reads and checks the fingerprint and gives the person authentication that the fingerprint thus read is his fingerprint that is registered in advance in the authentication apparatus.

However, those authentication apparatuses using a fingerprint have a problem that a third parson can pretend to be a person whose fingerprint is registered in advance in the authentication apparatus by making a copy of the fingerprint of the registered person with a certain means and having the copied fingerprint read by a fingerprint reading portion of the authentication apparatus.

To solve this problem, an authentication apparatus using a wrinkle pattern on the surface of an iris of a human was proposed as an authentication apparatus capable of performing authentication in a non-contact state (Electronics, 1998 February issue, Ohmsha, Ltd.). However, even this authentication apparatus using an iris has a problem that a third person can be authenticated by pretending to be a person who is registered in the authentication apparatus by making a copy of a wrinkle pattern on the surface of an iris by illegally photographing the eye of the registered person and using glasses to which the copy is stuck.

The authentication apparatus using data that is generated based on an iris that is part of a human body has an absolute advantage for identification of an individual that every parson has irises that are different from those of all of the other persons and do not vary in all of his life. Further, such an authentication apparatus is superior by nature in recognition ability as a means for recognizing an individual in a non-contact state. However, as described above, it has the problem that a third person can pretend as a registered person by making a copy of an iris of the registered person with a certain means and using it.

SUMMARY OF THE INVENTION

The present invention has been made in view of the above circumstances in the art, and an object of the invention is therefore to increase the authentication accuracy of an authentication apparatus using an iris by making it possible to check whether data of an iris that is registered for authentication in the iris authentication apparatus or data of an iris to be authenticated is one obtained from a living body and thereby prevent a third person to pretend as a registered person (living body) by using iris data that is not obtained from a living body.

The invention provides an iris authentication apparatus which performs authentication based on data generated from an iris, comprising iris data detecting means for detecting a state of an iris in the form of data; living body detecting means for detecting whether the iris state is in a living body state; and judging means for judging that the data detected by the iris data detecting means is effective when the living body detecting means has detected that the iris state is in a living body state. The iris authentication apparatus having this configuration can reliably prevent a third person from being authenticated instead of a registered person by forging an iris pattern.

The invention also provides an iris authentication apparatus which performs authentication based on data generated from an iris, comprising iris data detecting means for detecting a state of an iris in the form of data; storing means for storing the data representing the iris state detected by the iris data detecting means; living body detecting means for detecting whether the iris state is in a living body state based on the data stored in the storing means and representing the iris state; and judging means for judging that the data detected by the iris data detecting means is effective when the living body detecting means has detected that the iris state is in a living body state. The iris authentication apparatus having this configuration can reliably prevent a third person from being authenticated instead of a registered person by forging an iris pattern.

DETAILED DESCRIPTION OF THE PREFERRED EMBODIMENT

An iris authentication apparatus according to an embodiment of the present invention will be hereinafter described with reference to FIGS. 1–5.

First, the structure of a human eyeball will be described with reference to FIGS. 4 and 5.

Figure 4:
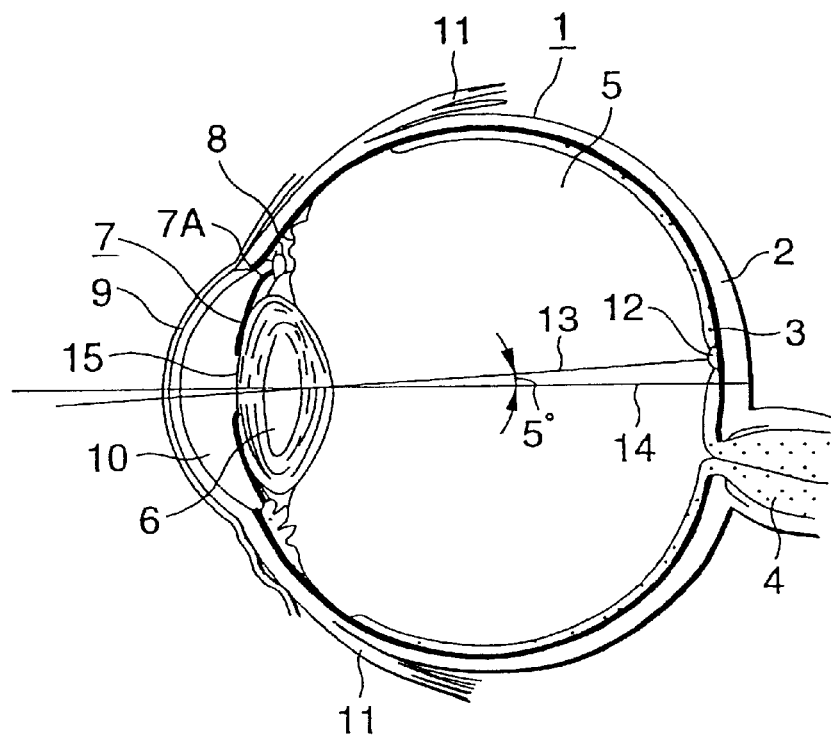
FIG. 4 is a sectional view of a human eye.
Figure 5:
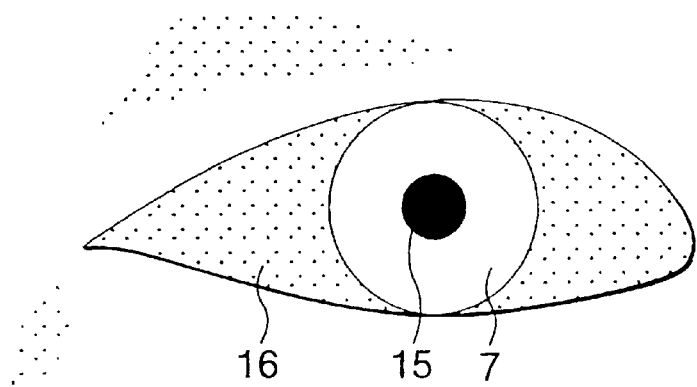
FIG. 5 is a front view of a human eye.

FIG. 4 shows the main part of a human eyeball 1, which is made of a sclera 2, a retina 3, an optic nerve 4, a vitreous body 5, a lens 6, an iris 7, a ciliary body 8, a cornea 9, an anterior chamber 10, ocular muscles 11, a fovea 12, and a pupil 15.

Reference symbol 7A denotes the surface of the iris 7, 13 denotes a visual axis connecting the center of the lens 6 and the fovea 12, and 14 denotes the optical axis of the lens 6. The visual axis 13 intersects the optical axis 14 at the center of the lens 6 and is rotated from the optical axis 14 counterclockwise by about 5°.

The iris 7 is composed of a sphincter and a dilatator that adjust the degree of opening of the pupil 15. Chaos-like wrinkles are formed on the surface 7A of the iris 7 so as to develop from the periphery of the pupil 15 outward. Since the chaos-like wrinkles are formed based on randomness in human growth, they have a pattern that is specific to each person and even the right and left eyes of the same person have different wrinkle patterns. Further, the wrinkle pattern of a person stops changing several years after his birth and thereafter does not change until his death.

Next, a description will be made of an example of a method for checking, in performing authentication with the authentication apparatus of this embodiment using iris information that is based on an iris wrinkle pattern, whether the iris information is one obtained from a living body by detecting whether the iris information has a property that is specific to a living body.

First, a description will be made of cycloversions and a variation of the pupil 15 that are examples of iris information that can be used for detecting whether iris information has a property specific to a living body.

The term "living body" means a human who is alive and active at a time point of detection as to whether iris information has a property specific to a living body.

The cycloversions are eyeball movements that are defined as follows.

The cycloversions are two kinds of eyeball movements. The first movement is an eyeball movement that is caused by vestibulo-ocular reflex (VOR) that occurs based on information generated by the equilibrium sensing system such as the semicircular canals of a human when his body is moved so that an incident image formed on the retina 3 is rotated about the visual axis 13. This is a rotational movement about the visual axis 13 to compensate for the rotation of the image formed on the retina 3, and is called a rotational eyeball movement. The second movement is also a rotational eyeball movement that is caused by optokinetic nystagmus (OKN) that occurs in response to information coming from the visual system.

The cycloversion caused by VOR is a living body reaction movement that is characterized in that when, for example, the head is rotated about the visual axis 13 in darkness, a rotational eyeball movement is caused by a movement of the ocular muscles 11 in the opposite direction by about 1/10 of the rotation angle of the head. On the other hand, the cycloversion caused by OKN in response to information coming from the visual system is a living body reaction movement that is characterized in that the gain is as low as about 0.003 and the variation is large.

The diameter of the pupil 15 that is enclosed by the iris 7 is controlled by action of the sphincter that is part of the iris 7 and contributes to miosis (or contraction) and a dilatator that is also part of the iris 7 and contributes to mydriasis (or enlargement).

It is said that the miosis movement is mainly dominated by the parasympathetic nervous system and the mydriasis is mainly dominated by the sympathetic nervous system. There is a feature of a living body reaction that the diameter of the pupil 15 always varies reflecting activities (also called fluctuations) of those nervous systems. There is another feature that the amplitude of the variation is larger when the frequency of a variation frequency component of the activities of those nervous systems is lower; the amplitude variation is close to the 1/f characteristic where f is the frequency of a variation frequency component.

The pupil 15 that is enclosed by the iris 7 has a function equivalent to the diaphragm of a camera. There is a living body reaction that the pupil 15 contracts as the intensity of light entering the pupil 15 increases. The latency of miosis (that is, the time from occurrence of an optical stimulus to the pupil 15 to start of actual miosis) and the time from reduction in the intensity of light entering the pupil 15 to start of actual mydriasis have a feature that they fall within standard ranges in the case of a person with a normal, healthy body.

Next, an example of a method for making it possible to check whether iris information is one obtained from a living body by using the features of the cycloversions will be described with reference to FIGS. 1–3.

Figure 1:
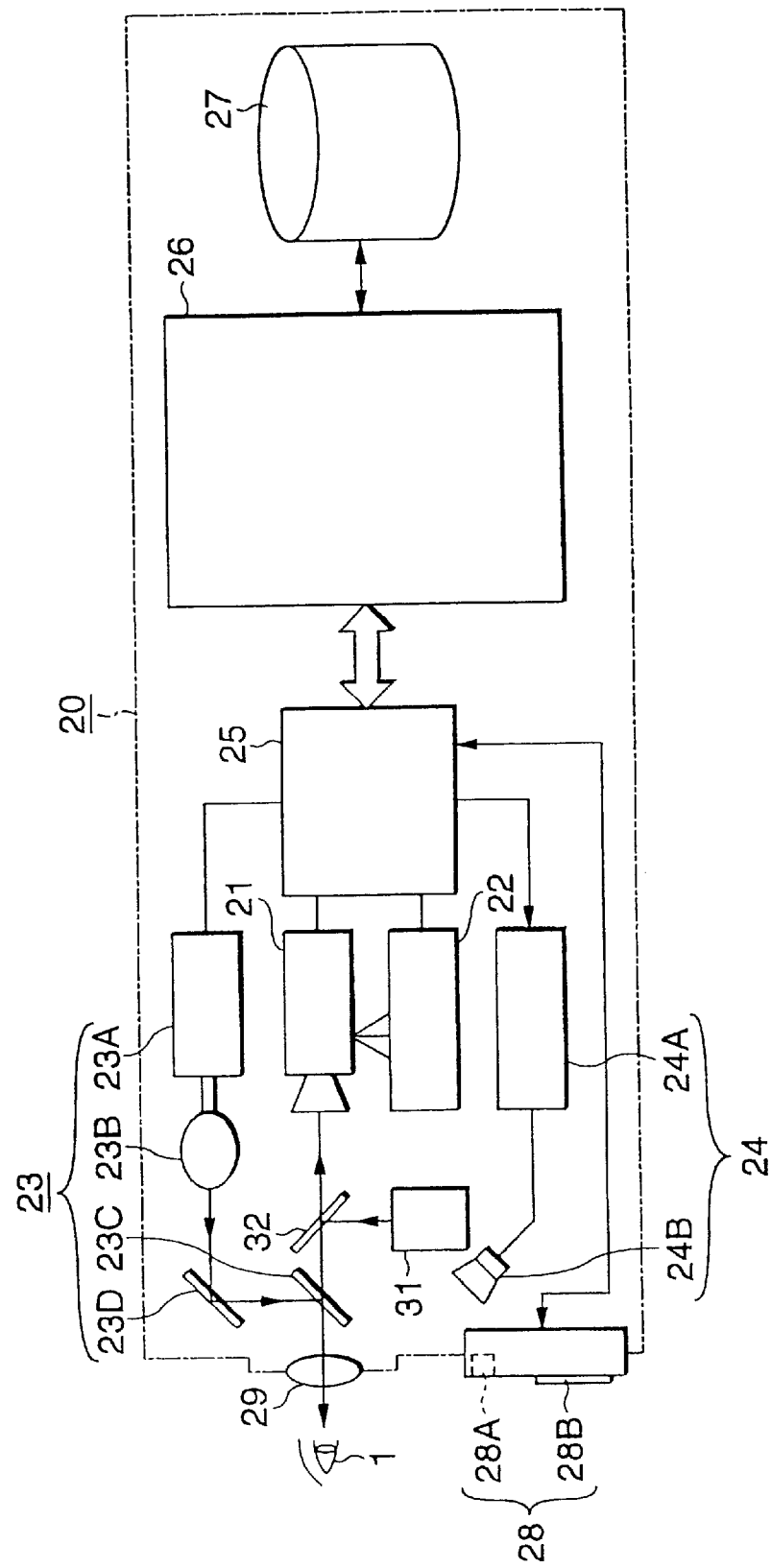
FIG. 1 is a block diagram showing an example configuration of an iris authentication apparatus according to the invention.

FIG. 1 is a block diagram showing the configuration of the main part of an iris authentication apparatus according to this invention. The iris authentication apparatus 20 is composed of a camera section 21, a mechanics control section 22, a light source section 23, a sound reproduction section 24, a signal processing section 25, an iris data processing section 26, a database section 27, an input/display section 28, an optical lens 29, a monitor 31, and a half mirror 32.

The light source section 23 is composed of an illumination controller 23A, a lamp 23B, a half mirror 23C, and a full-reflection mirror 23D. The sound reproduction section 24 is composed of a reproduction controller 24A and a speaker 24B. The input/display section 28 is composed of a ten-key pad 28A and a data display 28B.

Figure 2:
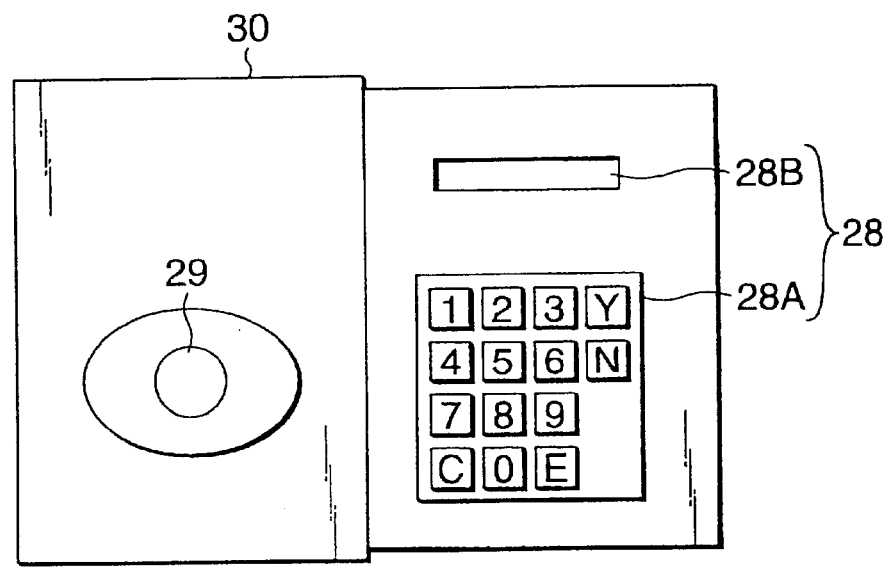
FIG. 2 is a front view showing an appearance of the iris authentication apparatus of FIG. 1.
Figure 3:
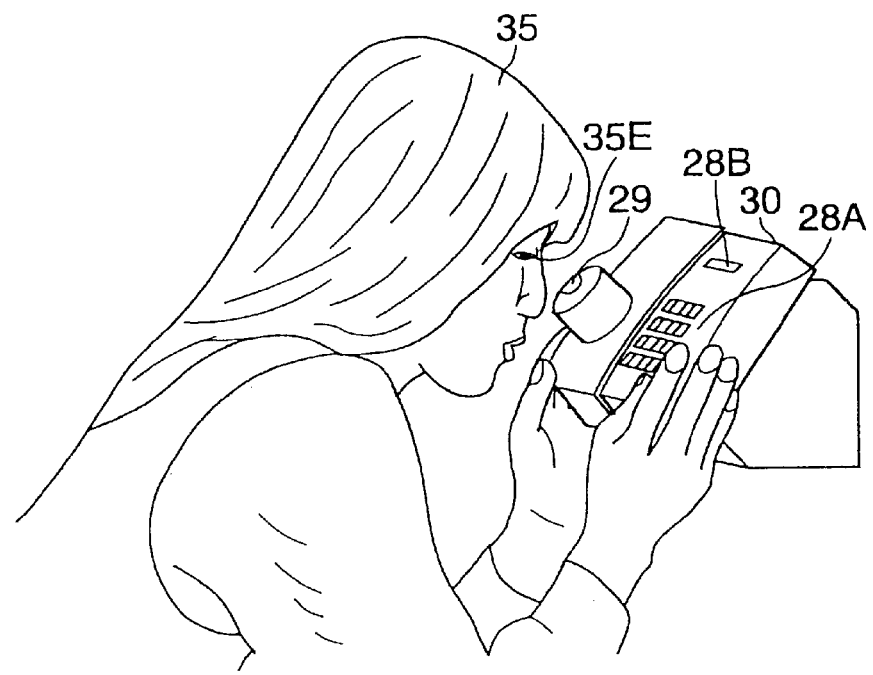
FIG. 3 is a perspective view showing how the iris authentication apparatus of FIG. 1 is used.

FIG. 2 is a front view showing an appearance of the iris authentication apparatus 20 of the invention and FIG. 3 is a perspective view showing how the iris authentication apparatus 20 is used. In FIGS. 2 and 3, reference numeral 30 denotes a body of the iris authentication apparatus 20. In the iris authentication apparatus 20, the optical lens 29 is disposed at such a position as to be easily viewed by a person 35 who intends to be authenticated (hereinafter referred to as "subject person"). The ten-key pad 28A and the data display 28B, which constitute the input/display section 28, are disposed at such a position as to be easily used and recognized by the subject person 35 on the body 30.

Next, the operation of the iris authentication apparatus 20 will be described.

The signal processing section 25 controls the illumination controller 23A so that the lamp 23B emits visible light. The visible light is passed through the full-reflection mirror 23D, the half mirror 23C, and the optical lens 29, and focused by the optical lens 29 at the viewing position of the subject person 35 that is outside the body 30.

In this state, as shown in FIG. 3, the subject person 35 views the optical lens 29 with his right eye 35E, for example. Further, in this state, the subject person 35 adjusts the position of his right eye 35E so that he sees the visible light right ahead and the camera section 21 is focused on the right eye 35E. An iris detection mode operation is performed in this state. That is, the right eye 35E of the subject person 35 that consists of the iris 7, the pupil 15, and the white 16 of the eye (see FIG. 5) is shot and its image data is generated by the camera section 21. The image data of the eye is supplied from the camera section 21 to the signal processing section 25.

In the iris detection mode operation, the signal processing section 25 judges whether the right eye 35E of the subject person 35 is located at a prescribed position with respect to the optical lens 29. If it is judged that the right eye 35E is not located at the prescribed position, the signal processing section 25 may control the reproduction controller 24A so that the subject person 35 hears a guide message that is generated by speech synthesis and output from the speaker 24B and moves so that his right eye 35E of the subject person 35 is located at the prescribed position with respect to the optical lens 29.

Image data of the right eye 35E of the subject person 35 that is obtained in a state that the right eye 35E is located at the prescribed position with respect to the optical lens 29 is supplied from the camera section 21 to the signal processing section 25. The signal processing section 25 cuts out data of the surface 7A of the iris 7 from the image data of the right eye 35E, generates feature extraction data by performing feature extraction processing for extracting features of the surface 7A from the cut-out data of the surface 7A, and supplies the generated feature extraction data to the iris data processing section 26.

The iris data processing section 26 compares the feature extraction data with another feature extraction data of the surface 7A of the iris 7 of the right eye 35E of the subject person 35 that was registered in advance in the database section 27 and tries to make matching between the two data. If as a result of this processing the level of matching between the two data falls within a predetermined range, the iris processing section 26 judges that the subject person 35 can be the registered person. If the level of matching between the two data does not fall within the predetermined range, the iris data processing section 26 judges that the subject person 35 is not the registered person.

The feature extraction data to be registered in the database section 27 is not limited to feature extraction data of the right eye of a subject person and may be that of his left eye or both of his eyes.

If the judgment result is that the subject person 35 can be the registered person, the process goes to a step of checking, by using the VOR cycloversion, whether the iris information is one obtained from a living body.

In this step, the lamp 23B is switched to a lamp that radiates near infrared light that is undetectable by human eyes. Further, the camera section 21 may be one that is sensible also in the near infrared range or switching may be made in the camera section 21 before this step starts from a state that the camera section 21 is sensible in the visible range to a state that it is sensible in the near infrared range.

The lamp 23B is lit and emits near infrared light, and iris detection mode setting is established with the subject person 35, that is, the right eye 35E of the subject person 35 is placed at the prescribed position with respect to the optical lens 29. In this state, the head of the subject person 35 is rotated by a prescribed angle and the right eye 35E is shot by the camera section 21 in the rotated state. Image data of the surface 7A of the iris 7 is generated by the signal processing section 25 and position data of this image is supplied to the iris data processing section 26.

The iris data processing section 26 determines difference position data between position data of the image data of the surface 7A of the iris 7 that was used in judging whether the subject person 35 is the registered person and the position data obtained this time in the state that the head is rotated by the prescribed angle.

If external light is obstructive to the check using the VOR cycloversion, a member for interrupting the external light, such as an eye-cap, may be attached to the optical lens 29.

Then, the difference position data is fed back from the iris data processing section 26 to the signal processing section 25. The signal processing section 25 controls the mechanics control section 22 so that the camera section 21 is rotated in such a direction that the difference position data is minimized. The iris data processing section 26 determines difference data in this state.

When the iris data processing section 26 has determined the minimum different data, a rotation angle, a rotation direction, etc. of the camera section 21, that is, eyeball movement data that is necessary to recognize a movement of the eyeball 1 of the subject person 35 that occurs to compensate for a rotation of the image formed on the retina 3 of the eyeball 1 that is caused by the rotation about the visual axis 13, is supplied from the mechanics control section 22 to the iris data processing section 26 via the signal processing section 25.

The iris data processing section 26 calls data relating to the features of the VOR cycloversion that is stored in advance in the database section 27. Based on this data, the iris data processing section 26 performs comparative analysis on the features of the eyeball movement data and judges whether the eyeball movement data is data obtained from a living body.

If the iris data processing section 26 has judged that the eyeball movement data is data obtained from a living body, the iris authentication apparatus 20 then judges that it is highly probable that the subject person 35 is the registered person, taking into consideration the previous judgment that the subject person 35 can be the registered person, which judgment was made based on the feature extraction data of the surface 7A of the iris 7.

Therefore, the iris authentication apparatus 20 is free of the problem that occurs in the case where whether the subject person 35 is the registered person is judged based on only feature extraction data of the surface 7A of the iris 7. That is, when the subject person 35 forges features of the surface 7A of the iris 7 by copying or the like and pretends to be the registered person, the iris authentication apparatus 20 can easily pierce such an act.

In the above-described example, whether data of the surface 7A of the iris 7 detected from the subject person 35 is living body reaction data obtained from a living body is judged by using the VOR cycloversion. A description will now be made of an example in which whether data of the surface 7A of the iris 7 detected from the subject person 35 is living body reaction data obtained from a living body is judged by using the OKN cycloversion.

This is done in the following manner. As shown in FIG. 1, the monitor 31 and the second half mirror 32 are provided. The iris authentication apparatus 20 is so configured as to present still images that rotate about the visual axis 13 to the right eye 35E (or the left eye) of the subject person 35 from the monitor 31 when an iris detection mode operation is performed in which image data of the right eye 35E (or the left eye) of the subject person 35 is supplied from the camera section 21 to the signal processing section 25 in the state of FIG. 3.

A signal obtained from the camera section 21 in a state that still images that rotate about the visual axis 13 are presented to the right eye 35E (or the left eye) of the subject person 35 is supplied to the signal processing section 25. Based on the data of the surface 7A of the iris 7 detected from the subject person 35, the signal processing section 25 generates optokinetic nystagmus (OKN) data for the still images rotating about the visual axis 13.

While the generated OKN data is supplied from the signal processing section 25 to the iris data processing section 26, the iris data processing section 26 calls data relating to the features of the OKN cycloversion that is stored in advance in the database section 27. Based on the data thus called, the iris data processing section 26 analyzes the features of the OKN data that has been supplied from the signal processing section 25 to the iris data processing section 26 and judges whether it is living body reaction data obtained from a living body.

If the iris data processing section 26 has judged that the OKN data has the features of the OKN cycloversion, the iris authentication apparatus 20 then judges that it is highly probable that the subject person 35 is the registered person.

Therefore, when the subject person 35 forges features of the surface 7A of the iris 7 by copying or the like and pretends to be the registered person, the iris authentication apparatus 20 can easily pierce such an act in the case where whether data of the surface 7A of the iris 7 detected from the subject person 35 is living body reaction data obtained from a living body is judged by using the OKN cycloversion as in the case the same judgment is performed by using the VOR cycloversion.

In the above-described examples, whether data of the surface 7A of the iris 7 detected from the subject person 35 is living body reaction data obtained from a living body is judged by using the VOR cycloversion or the OKN cycloversion.

However, in the embodiment, this judgment may also be performed by using the features of a variation in the diameter of the pupil 15 that the diameter of the pupil 15 always varies reflecting activities of the sympathetic and parasympathetic nervous systems in a state that the miosis movement of the pupil 15 is mainly dominated by the parasympathetic nervous system and the mydriasis movement of the pupil 15 is mainly dominated by the sympathetic nervous system and that the amplitude of the variation is larger when the frequency of a variation frequency component of the activities of those nervous systems is lower; the amplitude variation is close to the 1/f characteristic where f is the frequency of a variation frequency component.

As a further alternative, whether data of the surface 7A of the iris 7 detected from the subject person 35 is living body reaction data obtained from a living body may be judged by using features of a variation during latency and a recovery process of an optical reaction in the iris 7 in response to an optical stimulus to the iris 7.

Further, the iris authentication apparatus 20 of the embodiment may be configured in the following manner. In a state that a spot image is presented to the subject person 35 from the monitor 31 via the second half mirror 32, the brightness of the spot image is varied. Iris contraction that accompanies a pupil diameter variation in response to the brightness variation is judged based on an output signal of the camera section 21. If such a variation is found, it is judged that the iris 7 of the subject person 35 is of a living body.

Still further, whether the iris 7 of the subject person 35 is of a living body may be judged based on the dynamic vestibulo-ocular reflex, that is, an eyeball movement control ability of a human that a human recognizes a movement direction of his head with the equilibrium sensing organ, sends a signal corresponding to a recognition result to the muscles for controlling the eyeball movement via the nerves, and causes the eyeballs to move in the opposite direction to the head movement direction, so as to be able to continue looking at properly an object that he looked at before the head movement.

In this case, a gyro section as a sensor for detecting a rotation angle of the camera section 21 is provided in the mechanics control section 22 for the camera section 21. In a state that a spot image is presented to the subject person 35 from the monitor 31 via the second half mirror 32, the head of the subject person 35 is rotated in the right-left direction, for example. The camera section 21 is caused to automatically follow a movement of the iris 7 of the subject person 35.

Movement data is obtained by detecting this movement with the gyro section. If the value of the data obtained is smaller than data that is prepared in advance as a reference value, it is judged that the iris 7 of the subject person 35 is of a living body.

Further, in the embodiment, whether the iris 7 of the subject person 35 is of a living body may be judged based on, in addition to an iris movement as just described, iris contraction that was also described above. That is, the brightness of a spot image is varied and iris contraction that accompanies a pupil diameter variation in response to the brightness variation is judged based on an output signal of the camera section 21. If such a variation is found, it is judged that the iris 7 of the subject person 35 is of a living body.

This double judgment makes it possible to pierce even an act of the subject person 35 who illegally photographs the iris of another person to obtain a copied iris pattern and uses a contact lens to which the copied iris pattern is attached.

Iris authentication may be performed more correctly in the following manner. One or some of data based on the VOR cycloversion, data based on the OKN cycloversion, and living body reaction data that is characterized in optical reaction of an iris are registered in advance in the database section 27 for each person who will need authentication in such a manner that different kinds of data are registered for different persons. The iris authentication apparatus 20 is so configured as to be able to judge whether eyeball movement data of a person who intends to be authenticated is living body reaction data obtained from a living body based on corresponding data specific to the registered person.

Although in the examples of FIGS. 1–3 the iris authentication apparatus 20 has a single body, the iris data processing section 26 and the database section 27 may be separated from the other part of the iris authentication apparatus 20 and provided and managed in a management center or the like.

In this case, it is possible that a plurality of the other parts of the iris authentication apparatuses 20 are placed at a plurality of locations such as entrance/exit gates, respectively, and connected to the iris data processing section 26 and the database section 27 that are provided in a management center or the like so as to be managed in a concentrated manner.

As described above, in authenticating a person based on his iris, the invention makes it possible to judge whether his iris of a living body. Therefore, the invention can reliably prevent a third person from being authenticating by pretending to be a registered person by forging an iris pattern and using it.

What is claimed is:

1. An iris authentication apparatus that performs personal authentication based on data generated from an iris of a person's eye the apparatus comprising:

iris data detecting means including a camera for detecting an iris of a person and producing corresponding detected iris data;

iris data processing means for judging that the iris data detected by the iris data detecting means is iris data of a registered person by comparing the detected iris data with registered iris data; and means for detecting that the detected iris data is detected from a living person including a light source for radiating near infrared light to the person's eye, a signal processor for processing an output of the camera, and a mechanical controller for adjusting a position of the camera, whereby a rotation of the head of the person results in an involuntary movement of the eye and position data of the iris image detected by the camera is fed to the iris data processing means that determines difference position data between the iris data used to judge the registered person and current position data upon the head rotation and the difference position data is fed to the signal processor to produce a control signal fed to the mechanical controller to move the camera to minimize the difference position data, wherein the iris data processing means compares the minimized position data with stored position data and it is judged whether a living person is present.

2. An iris authentication apparatus which performs authentication based on data generated from an iris, the apparatus comprising:

iris data detecting means including a camera for detecting an iris and producing corresponding iris data;

an iris processor including storing means for storing the iris data representing the iris detected by the iris data detecting means for judging that the iris data from the iris data detecting means is iris data of a registered person; and living body detecting means for detecting whether the iris is in a living person including a light source for radiating near infrared light to the person's eye, a signal processor receiving an output from the camera, and a mechanical controller for adjusting a position of the camera whereby a rotation of the head of the person results in an involuntary movement of the eye and position data of the iris image detected by the camera is fed to the iris data processor that determines difference position data between the iris data used to judge the registered person and current position data upon the head rotation and the difference position data is fed to the signal processor to produce a control signal fed to the mechanical controller to move the camera to minimize the difference position data, wherein the iris data processor compares the minimized position data with stored position data and it is judged whether a living person is present.

\* \* \* \* \*